United States Patent [19]

Salpekar et al.

[11] Patent Number: 4,600,579

[45] Date of Patent: Jul. 15, 1986

[54] N-ACETYL-P-AMINOPHENOL COMPOSITIONS CONTAINING PARTIALLY GELATINIZED STARCH AND METHOD FOR PREPARING SAME

[75] Inventors: Anil M. Salpekar, Creve Coeur; Steven R. Freebersyser, Florissant; Douglas A. Robinson, Creve Coeur, all of Mo.

[73] Assignee: Mallinckrodt, Inc., St. Louis, Mo.

[21] Appl. No.: 502,067

[22] Filed: Jun. 7, 1983

[51] Int. Cl.⁴ .................. A61K 31/16; A61K 31/70
[52] U.S. Cl. ........................................ 424/80; 514/629
[58] Field of Search ........................... 424/80; 514/629

[56] References Cited

U.S. PATENT DOCUMENTS

| | | | |
|---|---|---|---|
| 2,798,838 | 7/1957 | Robinson | 167/82 |
| 2,876,160 | 3/1959 | Schoch et al. | 167/82 |
| 3,181,998 | 5/1965 | Kanig | 167/82 |
| 3,499,962 | 3/1970 | Wurzburg et al. | 424/35 |
| 3,786,123 | 1/1974 | Katzen | 264/53 |
| 3,851,032 | 11/1974 | Andrews et al. | 264/109 |
| 3,923,974 | 12/1975 | Andrews et al. | 424/80 |
| 4,072,535 | 2/1978 | Short et al. | 106/210 |

FOREIGN PATENT DOCUMENTS

| | | |
|---|---|---|
| 0011490 | 5/1980 | European Pat. Off. |
| 0040472 | 11/1981 | European Pat. Off. |
| 0070970 | 2/1983 | European Pat. Off. |
| 45-27111 | 9/1970 | Japan. |
| 1287431 | 8/1972 | United Kingdom. |
| 1390032 | 4/1975 | United Kingdom. |

OTHER PUBLICATIONS

"Polyplasdone XL ™ Tablet Disintegrant", GAF Corp. Bulletin No. 2302-099 (1980), 5 pages.
"PLASDONE ® Povidone USP," GAF Corp. Bulletin No. 2302-10 (1981), 14 pages (including covers).
Dr. rer. nat. Paul Heinz List, "Arzneiformenlehr", 1976, p. 74, original and translation (2 pages).
"LACTOSE-U.S.P. FAST-FLO," Foremost Foods Company brochure, 1977, 8 pages.
Salpekar, Anil M.; "A Study of Some Important Aspects of Tablet Lubrication"-Ph.D. Dissertation/Univ. Maryland; 1975; pages: title page, abstract (3 pages) and 189-204.
"Prototype Formulation: Acetaminophen Tablets", Colorcon, Inc. Technical Data bulletin (2/81), 2 pages.
"Evaluation of Starch 1500 as a Granulation Binder in the Formulation of Acetaminophen Tablets", Colorcon, Inc. Technical Data bulletin (2/81) 6 pages.
"Starch 1500 ™", Colorcon, Inc. brochure (1/81) 14 pages.

*Primary Examiner*—Stanley J. Friedman
*Attorney, Agent, or Firm*—R. G. Jackson; L. N. Goodwin; R. J. Klostermann

[57] ABSTRACT

An N-acetyl-p-aminophenol composition capable of being directly formed into a tablet having high hardness, short disintegration time and short dissolution time is disclosed. The composition includes N-acetyl-p-aminophenol, a pharmaceutically acceptable partially gelatinized starch, a pharmaceutically acceptable lubricant, water and optionally an auxiliary binder, an auxiliary disintegrant or both of these optional components. Also disclosed is a method for preparing the essential components (and optional components if desired) and spray drying the slurry.

16 Claims, No Drawings

N-ACETYL-P-AMINOPHENOL COMPOSITIONS CONTAINING PARTIALLY GELATINIZED STARCH AND METHOD FOR PREPARING SAME

The present invention relates to an N-acetyl-p-aminophenol composition containing partially gelatinized starch, to a method for preparing the composition and to orally administerable analgesic tablets formed from the composition.

N-acetyl-p-aminophenol (hereinafter referred to sometimes as acetaminophen or simply APAP) is generally non-compressible, especially in forming orally administerable tablets.

Accordingly, there is a substantial need in the art for a direct tabletting, free-flowing particulate APAP composition capable of being directly formed into a tablet having high hardness, short disintegration time and short dissolution time.

It has now been found by practice of the present invention that such APAP composition can be formed.

Advantageously, the composition of the present invention can be directly formed into tablets by tablet operators without need for admixing tabletting adjuvants or aids.

In various embodiments of the present composition described hereinbelow, the mutually conflicting needs for tablets having high hardness and low disintegration and/or dissolution times can be met.

DESCRIPTION OF THE INVENTION

Generally stated, the present invention provides a direct tabletting, free-flowing particulate pharmaceutical composition capable of being directly formed into a tablet having high hardness, short disintegration time, and short dissolution time, the composition comprising as components thereof:
  (A) N-acetyl-p-aminophenol,
  (B) a pharmaceutically acceptable partially gelatinized starch having a Percent Gelatinization of from about 50 to about 75% and in an amount effective for imparting said hardness, disintegration time and dissolution time,
  (C) a pharmaceutically acceptable lubricant in an amount at least sufficient to impart effective mold release properties to said tablet, and
  (D) water in an amount from about 0.5 to about 1.5% based on the total weight of the composition, said components being distributed throughout the particles of said composition in at least approximately the same distribution achieved when the composition is prepared by spray drying an aqueous slurry including said components (A), (B), and (C).

In another aspect, generally stated, this invention provides a method for preparing a direct tabletting, free-flowing particulate N-acetyl-p-aminophenol composition capable of being directly formed into a tablet having high hardness, short disintegration time and short dissolution time, said method comprising:
  (a) forming a slurry containing components dispersed substantially uniformly throughout an aqueous medium, said components comprising:
    (A) N-acetyl-p-aminophenol,
    (B) a pharmaceutically acceptable partially gelatinized starch having a Percent Gelatinization of from about 50 to about 75% and in an amount effective for imparting said hardness, disintegration time and dissolution time,
    (C) a pharmaceutically acceptable lubricant in an amount at least sufficient to impart effective mold release properties to said tablet,
  (b) spray drying said slurry under spray drying conditions such that the spray dried particles include water an amount from about 0.5 to about 1.5% based on the total weight of the composition, said components being distributed throughout the particles of said composition such that at least a portion of said lubricant is dispersed within said particles and at least a portion of the lubricant is disposed on the outer surfaces of said particles.

In yet another aspect, generally stated, this invention provides an orally administerable analgesic tablet formed from the pharmaceutical composition described above.

DETAILED DESCRIPTION OF THE INVENTION AND OF THE MANNER AND PROCESS OF MAKING AND USING IT

The N-acetyl-p-aminophenol component of the present invention is preferably provided in finely defined form, i.e., the APAP is preferably of small particle size. For example, it has been found that if more than 50% by weight of the APAP particles are larger than 200 mesh (U.S. standard sieve) then the spherical conformation of the particles of the composition is adversely affected. For use in the present invention, preferably all of the APAP particles will pass through a 200 mesh screen, more preferably 75% will pass through a 325 mesh screen and most preferably all will pass through a 325 mesh screen.

The partially gelatinized starch component of the direct tabletting composition has a Percent Gelatinization of from about 50 to about 75%. As used herein, the term "Percent Gelatinization" is a measure of the extent of gelatinization of the partially gelatinized starch relative to fully gelatinized starch and means the percent of Starch 1551 by National Starch Company (a fully gelatinized starch) required in a two-component mixture thereof with fully non-gelatinized corn starch such that the value of spectrophotometric absorbance for the mixture at a wavelength of 340 nanometers is the same as the spectrophotometric absorbance value exhibited at such wavelength for the partially gelatinized starch being characterized as having a given value (%) of Percent Gelatinization, subject to the provisos (1) that the absorbance values for both such mixture and such partially gelatinized starch (PGS) are measured on samples prepared therefrom by the modified-Shetty procedure described hereinbelow and (2) that the percentage amount of moisture in the sample prepared from such PGS is at least substantially the same as that in the sample prepared from such mixture.

The modified-Shetty procedure referenced above is a modification of the procedure for determining the degree of starch gelatinization set forth in Shetty et al., "Determining the Degree of Starch Gelatinization," *Cereal Chemistry*, Vol. 51, No. 3, pp. 364–375 (1974), incorporated herein by reference. Briefly stated, the procedure set forth in the above-cited Shetty et al. article includes selective digestion of the starch with DIAZYME ® glucoamylase (Miles Laboratories) to release D-glucose, working-up the digested starch, treating the digested and worked-up starch with Worthington Reagent to impart spectrophotometric absorbancy to the treated starch and subjecting the resulting sample to spectrophotometry. In the modified-Shetty procedure the following modifications are employed:

(1) Initially, three portions of the starch are washed with 100 ml methanol and passed through a 5-micron Millipore filter. The washed starch portions are dried for about 16 hours at 50° C. prior to weighing and assaying.

(2) The glucoamylase starch digestion is incubated at 50° C. for 30 minutes.

(3) The spectrophotometric absorbancy is measured at a wavelength of 340 nanometers for each of the three treated portions of the starch and the arithmetic mean of the three absorbance measurements is taken as the "absorbance value" recited above.

Approximate Percent Gelatinization values can be conveniently determined using a correlation graph generated for the following starch standards: fully non-gelatinized corn starch (containing zero % gelatinized starch), fully gelatinized starch (Starch 1551-National), and a set of binary mixtures thereof containing different known amounts of the fully gelatinized starch. For example, absorbance was determined by the modified-Shetty method for a set of standards including such starches individually and binary mixtures thereof containing 20%, 40%, 60% and 80% of Starch 1551. The results were plotted on Cartesian coordinates and showed a substantially linear relationship between the amount, in percent, of fully gelatinized starch and the corresponding absorbancy. Three data-generation runs were made, with correlation factors found for the three runs of 0.9926, 0.9974 and 0.9952. The final correlation graph was a plot of the three-run average absorbances found for each of the six gelatinized starch amounts (0, 20, 40, 60, 80 and 100%) versus such amounts. The spectrophotometric samples prepared from each such standard had moisture contents in the range from about 3 to about 5%. Tests on spectrophotometric samples prepared from Starch 1500 (Colorcon, Inc.) had moisture contents in the 3 to 5% range and the Percent Gelatinization of that herein preferred partially gelatinized starch was approximated as 57.7%, the value of % fully gelatinized starch on the final correlation graph for the average absorbance found for the samples prepared from Starch 1500.

The partially gelatinized starch (hereinafter referred to as PGS) serves to impart good binder and disintegrant properties as well as a good balance thereof to the composition, which can be directly tabletted to form tablets having high hardness, short disintegration time and short dissolution time.

The term "direct tabletting" and terms of like import, as used herein, mean that the composition can be formed into a tablet using well known tabletting apparatus and processes without need for addition of any adjuvant material to the composition. Inclusion of PGS having a Percent Gelatinization of less than about 50% (e.g., 45% or less) usually results in unacceptably lower compressibility (as evidenced, e.g., by unacceptably lower tablet hardness). Inclusion of PGS having a Percent Gelatinization of more than about 75% (e.g., 80% or more) usually results in unacceptably longer tablet disintegration time and/or unacceptably longer tablet dissolution time. The lower hardness, longer disintegration time and longer dissolution time are relative to the corresponding tablet hardness, disintegration and dissolution times obtained under identical tabletting conditions for otherwise identical compositions except that the Percent Gelatinization of the PGS component is within the above range.

The PGS is included in an amount effective for imparting to the composition the capability of being formed into tablets having high hardness (e.g., about 8 kp or more), short disintegration time (e.g., about 10 minutes or less) and short dissolution time (e.g., about 20 minutes or less for 80% or more of the APAP to dissolve).

As used herein, the term "kp" means kiloponds, a well known unit of force for expressing hardness or crushing strength of pharmaceutical tablets when such hardness is determined on a Schleuniger Tablet Hardness Tester.

In general, such effective amount of PGS is from about 5 or less to about 15 or more parts per 100 parts of the composition.

Advantageously and unexpectedly, tablets formed from the compositions of this invention are generally found to exhibit little or no variation in tablet disintegration time with variation in tablet hardness, especially in higher hardness ranges, e.g., from about 8 kp to about 15 kp and in some instances to about 20 kp. This substantial independence of disintegration time is highly advantageous in aiding tablet formulators to produce large commercial quantities of tablets of requisite disintegration time with minimal concern for tablet-to-tablet variations in hardness as typically result from the inherent limitations of tablet-forming equipment or human error of operators thereof.

Partially gelatinized starch suitable for use in the composition can be prepared using any suitable starch-gelatinization method and stopping the gelatinization when the desired Percent Gelatinization has been obtained. A suitable PGS is also commercially available from Colorcon, Inc., West Point, Pa. as Starch 1500 (preferred).

The lubricant component may be any pharmaceutically acceptable lubricant, which may be, e.g. hydrophilic or hydrophobic. This component is present in a lubricating amount at least sufficient to impart mold release properties to tablets formed of the compositions and preferably insufficient to increase disintegration time and dissolution time of such tablets, and preferably insufficient to decrease the hardness obtainable for tablets formed from compositions of this invention containing lower lubricating amounts of the same lubricant.

Suitable lubricants for use as the lubricant component include, for example, stearic acid; metallic stearate (such as sodium, calcium, magnesium and zinc stearate, etc.); sodium lauryl sulfate; polyethyleneglycol; hydrogenated vegetable oils; talc; and compatible mixtures of two or more such materials. Stearic acid is preferred.

In general, the stearic acid or other lubricant component may be present in an amount from about 0.10 to about 0.4%, preferably from about 0.15 to about 0.25%, based on the total amount of the composition. In order to avoid decreasing the hardness of the tablets formed from compositions including stearic acid, it is critical that the amount of stearic acid does not exceed about 0.25%.

The composition also includes water in an amount effective for aid in direct tabletting. Such effective amount is, in general, found to be from about 0.5 to about 1.5% based on the total weight of the composition, preferably about 1.0% on the same basis.

Optionally, the composition may further include a pharmaceutically acceptable compressibility-promoting binder as an additional binding agent in an amount effective for increasing the obtainable hardness of tablets formed from the composition.

Materials suitable for use as the optionally included, but preferably included additional binder agent include, for example, starch paste (fully gelatinized starch); pregelatinized starch (a fully gelatinized starch); polyvinylpyrrolidone; hydroxypropylmethylcellulose; hydroxypropylcellulose; gelatin; natural gums (e.g., gum acacia, gum tragacanth, etc.); sucrose; mannitol; ethylcellulose; synthetic polymer binders commonly used in the industry; and compatible mixtures of two or more such materials. Polyvinylpyrrolidone (PVP) is preferred (preferably PLASDONE ® PVP by GAF Corp.).

In general, such effective amount of optional binder is from about 0.5 or less to about 1.4 or more parts, preferably not more than 1.4, more preferably about 1.2 parts, per 100 parts of the composition.

Optional or auxiliary binders preferably are not included in an amount in excess of 25 parts per 100 parts of the PGS component, especially where fully gelatinized starch (pregelatinized or otherwise) is employed as the optional binder.

As a further option, the composition may further include a pharmaceutically acceptable disintegration-promoting material as an additional disintegration agent in an amount effective for decreasing the obtainable disintegration time of tablets formed from the composition.

Materials suitable for use as the optionally included, but preferably included, additional disintegration agent include, for example, starch (e.g., corn starch and other non-gelatinized starches); sodium carboxymethyl starch (sodium starch glycolate); microcrystalline cellulose; cross-linked cellulose; cross-linked polyvinylpyrrolidone; soy protein; alginic acid and compatible mixtures of two or more of such materials. Cross-linked polyvinylpyrrolidone (hereinafter referred to as XL-PVP), sometimes referred to in the art as cross-linked povidone, is preferred (preferably POLYPLASDONE XL ™ cross-linked N-vinyl-2-pyrrolidone from GAF Corporation).

In general, such effective amount of the optional or auxiliary disintegration agent is from about 1 or less to about 5 or more parts, preferably about 2.2 parts, per 100 parts of the composition.

In a number of important applications, it is desired that the APAP composition have the capability of being directly tabletted into tablets having a hardness of at least 12 kp (preferably at least 14 kp and, when formed into tablets having a hardness of 12 kp, such tablets to have a disintegration time of 5 minutes or less).

In general, such very high hardness/very low disintegration time compositions capable of being directly tabletted into tablets having a hardness of at least 12 kp, are provided by compositions embodying this invention wherein both the auxiliary binding agent and the auxiliary disintegration agent are included in amounts from about 0.5 to about 1.4 parts per 100 parts of the composition and from about 1 to about 5 parts on the same basis, such amounts being for the two optional agents in the order given.

In a preferred embodiment, a composition having such very high hardness and very low disintegration time includes the following components in the amounts indicated (together with water in an amount from about 0.5 to about 1.5% based on the total weight of the composition):

| COMPONENTS | APPROXIMATE AMOUNTS |
| --- | --- |
| APAP (acetaminophen) | 93-83 |
| Partially gelatinized starch | 5-10 |
| Stearic Acid | 0.1-0.4 |
| Polyvinylpyrrolidone | 0.5-1.4 |
| Cross-Linked Povidone | 1-5 |

The amounts shown are in parts per 100 parts (dry basis) of the composition.

The best embodiment composition of this invention contemplated at the time of executing this patent application is as follows, wherein the amounts given are in parts per 100 parts (dry basis) of the composition:

| COMPONENTS | APPROXIMATE AMOUNTS |
| --- | --- |
| APAP (acetaminophen) | 90 |
| Partially gelatinized starch | 6.45 |
| Stearic Acid | 0.15 |
| Polyvinylpyrrolidone | 1.2 |
| Cross-Linked Povidone | 2.2 |

The last-given embodiment includes water in an amount desirably from about 0.5 to about 1.5%, preferably about 1% based on the total weight (dry basis) of the composition. Such composition of the last-given embodiment can be repeatedly, in general, formed into tablets having hardness of 12 kp or more (often 14 kp or more) and having disintegration time of 5 minutes or less (often 4 minutes or less) at 12 kp hardness.

In use, the compositions of this invention advantageously may be composited with other active or inactive ingredients, either prior to compositing the components to form the composition or after the composition is formed (e.g., by dry blending the composition with such ingredients), and thereafter directly compressed into tablets having eminently suitable values of hardness and disintegration time for a variety of end-use applications.

The compositions of this invention are preferably made by the method set forth in the above section entitled "Description of the Invention", i.e., including a spray drying step.

The slurry preparation step is preferably carried out in a manner to achieve substantially complete hydration of the partially gelatinized starch component, preferably using a low shear mixing action so as not to increase the Percent Gelatinization of the PGS, at least not to increase it above the maximum desired percent gelatinization of about 75%. Preferably, the stearic acid is thoroughly mixed in the slurry, i.e., substantially uniformily dispersed throughout the aqueous medium (e.g., water) employed.

In the preferred embodiment of the method of this invention, the following procedure is followed.

Slurry Makeup (A) To a suitable blender add the partially gelatinized starch and an equal amount of acetaminophen. Thereafter, add a mixture of the stearic acid and cross-linked povidone with stirring until a uniform blend is obtained.

(B) Dissolve the polyvinylpyrrolidone in water, and, thereafter, to the resulting PVP solution add the blend from step A with agitation or mixing.

(C) To the mixture resulting from step B add the balance of the acetaminophen while mixing is continued.

(D) Preferably, the agitation is continued until the resulting slurry is smooth.

Spray drying conditions will be dependent on various factors, such as feed slurry concentration, method of atomization, type of spray dryer, desired rate of drying, relative humidity, and other factors which will be readily apparent to those skilled in the art.

Preferred spray drying conditions are set forth in the table below, along with an effective range of conditions for each condition or parameter indicated, by way of example for a counter-current spray dryer operated at a slurry feed rate of about 10 kilograms per hour:

Spray Drying Conditions

|  | Preferred | Range |
|---|---|---|
| Feed slurry concentration | 52% | 35-60% |
| Inlet temperature | 430° F. | 375° F.-600° F. |
| Outlet temperature | 200° F. | 150° F.-250° F. |
| Atomization pressure | 28 psi | 22-35 psi |
| Feed Pressure | 52 psi | 45-60 psi |

Practice of the present invention is illustrated by the following specific, but non-limiting examples. All amounts (including parts, %, etc.) given in the examples and throughout this disclosure, including the claims which follow, are by weight unless indicated otherwise.

Unless indicated otherwise, the compositions in each of the following Examples were prepared using the above described preferred method. This includes the steps of forming each slurry and spray drying the resulting slurry employing the preferred conditions set forth above or at least substantially such preferred conditions. Also, in each example unless indicated otherwise, spray drying was effected using counter current spray drying in a counter-current spray dryer manufactured by Niro Atomizer Company (Model No. 6903) in accordance with the manufacturer's instructions for use.

The PGS employed was Starch 1500 (Colorcon, Inc.) having an approximate Percent Gelatinization of 57.7%.

All tablets were formed on a Manesty B3B 16-station rotary tablet press (commercially available from Thomas Engineering Company) in accordance with the manufacturer's instructions for use. The press was fitted with a tablet tooling designed to make cylindrical tablets, each tablet having opposite bevel-edge flat faces and overall diameter of 13/32 inch. The press was operated to form tablets having a nominal weight of about 360 mg.

As used herein, the following terms have the meanings indicated:

(A) "disintegration time" means the time measured using the disintegration-time test method set forth in U.S. Pharmacoepia (hereinafter "USP") XX for uncoated tablets except that the disks are not employed;

(B) "dissolution time" means the time measured using the dissolution-time test method set forth in USP XX for APAP tablets;

(C) "hardness" means the hardness measured on a Schleuniger hardness tester;

(D) "maximum hardness" means the maximum hardness at which the tablets are substantially free of lamination;

(E) "friability" means the friability measured on a Roche Friabulator for 20 tablets and 100 revolutions.

In the Examples, unless otherwise indicated all tablet hardness values are averages for 10 tablets and all tablet weights are averages obtained by weighing 20 tablets as a whole and dividing by 20. Unless otherwise indicated, tablet disintegration times were measured for tablets having about 12 kp hardness.

EXAMPLES 1-3

Compositions of this invention were prepared following the example preparation method referenced above. Shown in the table below are the components employed in the indicated amounts, together with measured tabletting results (i.e., tablet hardness, disintegration time and dissolution time).

|  | APPROXIMATE AMOUNTS % (Dry Basis) | | |
|---|---|---|---|
| Component | Ex. 1 | Ex. 2 | Ex. 3 |
| APAP | 81.8 | 90 | 90 |
| PGS | 18.0 | 8.85 | 6.4 |
| (Percent Gelatinization) | (57.7) | (57.7) | (57.7) |
| Stearic Acid | 0.2 | 0.15 | 0.2 |
| Water | 1 | 1 | 1 |
| PVP (Aux. Binder) | — | 1.0 | 1.2 |
| XL-PVP (Aux. Disintegrant) | — | — | 2.2 |
| Tablet Results | | | |
| Hardness (kp) | 9.3 | 13 | 9.4 |
| Disintegration Time (Minutes) | 18.0 | 6 | 1.5 |
| Dissolution Time (T85) | — | — | (a) |

(a)less than 10 minutes

As indicated in these examples, Example 1 contains neither auxiliary binder nor auxiliary disintegrating agent; Example 2 includes an auxiliary binder but no auxiliary disintegrating agent; and Example 3 includes both an auxiliary binder and an auxiliary disintegrating agent. The disintegration time shown for Example 2 is for 13 kp hardness tablets.

EXAMPLES 4-8

Additional compositions of this invention were prepared following the example preparation method referenced above. Shown in the table below are the components employed (for each of these examples) in the indicated amounts, together with measured tabletting results (i.e., tablet hardness and disintegration time).

|  | Approximate Amounts % (Dry Basis) | | | | |
|---|---|---|---|---|---|
| Components | Ex. 4 | Ex. 5 | Ex. 6 | Ex. 7 | Ex. 8 |
| Acetaminophen | 90 | 90 | 90 | 90 | 90 |
| PGS | 7.75 | 5.45 | 5.4 | 4.45 | 4.45 |
| Lubricant System | | | | | |
| Stearic Acid | 0.15 | 0.15 | 0.1 | 0.15 | 0.15 |
| Sodium Lauryl Sulfate NF | 0.1 | — | 0.1 | — | — |
| Auxiliary Binder | 1.0 | 1.4 | 1.4 | 1.4 | 1.4 |

-continued

| Components | Approximate Amounts % (Dry Basis) | | | | |
|---|---|---|---|---|---|
| | Ex. 4 | Ex. 5 | Ex. 6 | Ex. 7 | Ex. 8 |
| Polyvinyl-pyrrolidone Auxiliary Disintegrant | | | | | |
| Microcrystalline Cellulose | 1.0 | — | 3.0 | — | — |
| Cross-Linked Cellulose | — | — | — | 1.0 | — |
| Corn Starch N.F. | — | 3.0 | — | 3.0 | 3.0 |
| Protein** | — | — | — | — | 1.0 |
| Tablet Results | | | | | |
| Hardness | 14 kp* | 14 kp* | 14 kp* | 14 kp* | 14 kp* |
| Disintegration Time | 3-5 min | 3-5 min | 3-5 min | 3-4 min | 3-4 min |

*greater than 14 kp
**"Emcosoy" (Edward Mendell Co.)

EXAMPLES 9-12

Examples 9-12 illustrate the unexpected relationship of maximum hardness to increasing amounts of stearic acid in the tabletted compositions when correspondingly decreasing amounts of PGS are employed.

Compositions of this invention were prepared following the example preparation method referenced above. Shown in the table below are the components employed in the indicated amounts, together with the maximum tablet hardness.

EXAMPLE 13

Example 13 illustrates advantageously and unexpectedly minor variation in tablet disintegration time with different tablet hardness values obtained for different extents of compression of each of the compositions of Examples 9-12 above.

Tabletting results are shown in the following table for Example 13, wherein the "Group" letters for each composition indicate different extents of compression as reflected by the hardness value for each Group.

Table for Example 13

| Composition | Group | Hardness (KP) | Disintegration Time (min.) | Friability (%) | Thickness (inches) | Weight (mg) |
|---|---|---|---|---|---|---|
| Example 9 | A | 10.1 | 1.42 | 0.54 | 0.169 | 364 |
| " | B | 12.4 | 1.55 | 0.41 | 0.164 | 362 |
| " | C | 13.8 | 1.55 | 0.41 | 0.160 | 362 |
| " | D | 19.4(a) | 3.30 | 0.27 | 0.154 | 366 |
| Example 10 | A | 9.4 | 1.30 | 0.55 | 0.170 | 362 |
| " | B | 11.7 | 1.55 | 0.27 | 0.164 | 362 |
| " | C | 16.0 | 2.10 | 0.42 | 0.158 | 360 |
| " | D | 18.5(a) | 3.00 | 2.2(b) | 0.154 | 360 |
| Example 11 | A | 8.1 | 1.55 | 1.15 | 0.167 | 361 |
| " | B | 13.2 | 2.50 | — | 0.160 | — |
| " | C | 14.3(a) | 4.15 | — | 0.159 | — |
| Example 12 | A | 7.8 | 2.00 | 1.35 | 0.174 | 371 |
| " | B | 9.7 | 1.30 | 0.61 | 0.163 | 360 |
| " | C | 13.4 | 4.00 | — | 0.160 | — |
| " | D | 14.5(a) | 1.35 | — | 0.160 | — |

(a) maximum hardness
(b) 2 of the 20 tablets were observed to be capped

| Component | APPROXIMATE AMOUNTS (% Dry Basis) | | | |
|---|---|---|---|---|
| | Ex. 9 | Ex. 10 | Ex. 11 | Ex. 12 |
| APAP | 90 | 90 | 90 | 90 |
| PGS | 6.45 | 6.4 | 6.3 | 6.2 |
| (Percent Gelatinization) | (57.7) | (57.7) | (57.7) | (57.7) |
| Stearic Acid | 0.15 | 0.2 | 0.3 | 0.4 |
| Water | 0.95 | 0.98 | 1.03 | 1.01 |
| PVP (Aux. Binder) | 1.2 | 1.2 | 1.2 | 1.2 |
| XL-PVP (Aux. Disintegrant) | 2.2 | 2.2 | 2.2 | 2.2 |
| Tablet Results | | | | |
| Maximum Hardness (kp) | 19.4 | 18.5 | 14.3 | 14.5 |

In another embodiment, the compositions of this invention can be prepared by co-current spray drying of slurries prepared as set forth above.

Preferred co-current spray drying conditions are set forth in the table below for a slurry feed rate of about 400 kilograms per hour, along with an effective range of conditions for each condition or parameter indicated:

Approximate Conditions

| | Preferred | Range |
|---|---|---|
| Feed slurry concentration | 53% | 35-60% |
| Inlet temperature | 520° F. | 300° F.-600° F. |
| Outlet temperature | 200° F. | 150° F.-250° F. |
| Atomization pressure | 2400-2800 psi | 1000-4000 psi |

EXAMPLE 14

In this example, the following preferred composition of this invention was prepared using substantially the same method employed in Examples 1-3 except co-current spray drying was employed at a slurry feed rate of approximately 400 kg/hr.

The composition is set forth below:

| Component | APPROXIMATE AMOUNTS % Dry Basis |
|---|---|
| APAP | 90 |
| PGS (Starch 1500 - Colorcon, Inc.) | 6.37 |
| Stearic Acid | 0.16 |
| Water | 0.90–0.97 |
| PVP (Aux. Binder) | 1.22 |
| XL-PVP (Aux. Disintegrant) | 2.24 |

The co-current spray dryer employed was an 8-foot Procter & Schwartz tower dryer equipped with an SF79 spray nozzle. The feed slurry concentration was about 53.2% solids. The dryer was operated at the following approximate conditions: inlet temperature (505°–510° F.), outlet temperature (196°–198° F.) and feed pressure or atomization pressure (2600 psig).

The resulting compositions had an approximate cumulative particle size distribution as follows:

| +60 mesh | +200 mesh | +325 mesh |
|---|---|---|
| 25.2–26.0% | 96.4–96.8% | 101.2% |

Tablets were prepared substantially as set forth above. Tablet properties (approximate values) obtained are set forth below for tablets compressed to different extents as in Example 13. The tablets had an average moisture content of about 1.13%.

| Group | Thickness (Inches) | Hardness (kp) | Weight (Grams) | Friability (%) | Disintegration Time (Min:Sec.) |
|---|---|---|---|---|---|
| 1 | 0.1704 | 9.4 | 0.364 | 0.41 | 3:05 |
| 2 | 0.1654 | 11.9 | 0.363 | 0.27 | 2:50 |
| 3 | 0.1605 | 13.6 | 0.362 | 0.41 | 3:30 |
| 4 | 0.1537 | 19.4 | 0.364 | 0.26 | (a) |

(a)Greater than 12 minutes

Dissolution times obtained for the tablets of Group 1 are shown by the following dissolution pattern showing the approximate amount of APAP which dissolved in the indicated time: 95.5% (6 minutes), 99.6% (12 minutes) and 99.4% (18 minutes.)

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A method for preparing a direct tabletting, free-flowing particulate N-acetyl-p-aminophenol composition capable of being directly formed into a tablet having high hardness, short disintegration time and short dissolution time, said method comprising:
    (a) forming a slurry containing components dispersed substantially uniformly throughout an aqueous medium, said components comprising:
        (A) N-acetyl-p-aminophenol in an analgesic amount,
        (B) a pharmaceutically acceptable partially gelatinized starch having a Percent Gelatinization of from about 50 to about 75% and in an amount effective for imparting said hardness, disintegration time and dissolution time, and
        (C) a pharmaceutically acceptable lubricant in an amount at least sufficient to impart effective mold release properties to said tablet, the total of the amounts of said components being such that the slurry concentration is approximately 35-60% by weight, and
    (b) spray drying said slurry under spray drying conditions such that the spray dried particles include water in an amount from about 0.5 to about 1.5% based on the total weight of the composition and such that the composition is at least substantially the same as a composition selected from the group consisting of (i) a first composition obtained when said slurry is co-currently spray dried at a slurry feed rate of about 400 kilograms per hour under the following approximate spray drying conditions: inlet temperature—300° F.–600° F., outlet temperature—150° F.–250° F. and atomization pressure—1000-4000 psi, and (ii) a second composition obtained when said slurry is counter-currently spray dried at a slurry feed rate of about 10 kilograms per hour under the following appromximate spray drying conditions: inlet temperature—375° F.–600° F., outlet temperature—150° F.–250° F., atomization pressure—22-35 psi and slurry feed pressure—45-60 psi,
said components being distributed throughout the particles of each of said first and second composiitions such that at least a portion of said lubricant is dispersed within said last-mentioned particles and at least a portion of the lubricant is disposed on the outer surfaces of said last-mentioned particles.

2. The method of claim 1 wherein the slurry is formed and maintained under forming and maintaining conditions including sufficiently low shear to avoid increasing said Percent Gelatinization above about 75%.

3. The method of claim 1 wherein said conditions under which said slurry is spray dried include co-current spray drying and the conditions set forth for said first compostion.

4. The method of claim 1 wherein said conditions under which said slurry is spray dried include counter-current spray drying and the conditions set forth for said second composition.

5. A direct tabletting, free-flowing particulate N-acetyl-p-aminophenol composition capable of being directly formed into a tablet having high hardness, short disintegration time, and short dissolution time, the composition comprising as components thereof:
    (A) N-acetyl-p-aminophenol in an analgesic amount,
    (B) a pharaceutically acceptable partially gelatinized starch having a Percent Gelatinization of from about 50 to about 75% and in an amount effective for imparting said hardness, disintegration time and dissolution time, (C) a pharmaceutically acceptable lubricant in an amount at least sufficient to impart effective mold release properties to said tablet, and (D) water in an amount from about 0.5 to about 1.5% based on the total weight of the composition, said components being distributed throughout the particles of said composition such that at least a portion of said lubricant is dispoersed within said particles and at least a portion of the lubricant is disposed on the outer surfaces of said particles, said composition prepared by the method of claim 1.

6. The composition of claim 5 further including a pharmaceutically acceptable compressibility-promoting binder as an additional binding agent in an amount effective for increasing the obtainable hardness of tablets formed from the composition, the slurry containing said binder in said-mentioned amount.

7. The composition of claim 5 further including a pharmaceutically acceptable disintegration-promoting material as an additional disintegration agent in an amount effective for decreasing the obtainable disintegration time of tablets formed from the composition, the slurry containing said material in said-mentioned.

8. The composition of claim 6 further including a pharmaceutically acceptable disintegration-promoting material as an additional disintegration agent in an amount effective for decreasing the obtainable disintegration time of tablets formed from the composition, the slurry containing said material in said-mentioned amount.

9. The composition of claim 5 wherein said Percent Gelatinization is about 60%.

10. The composition of claim 5 wherein said lubricant is stearic acid and included in an amount of not more than 0.25% based on the total weight of the composition.

11. The composition of claim 8 including from about 93–83% by weight of N-acetyl-p-aminophenol; from about 5 to about 15% by weight of said partially gelatinized starch; from about 0.1 to about 0.4% by weight of stearic acid as said lubricant; from about 0.5 to about 1.4% by weight of polyvinylpyrrolidone as said additional binding agent; and from about 1 to about 5% by weight of cross-linked povidone as said additional disintegration agent; based on 100% by weight of the composition exclusive of water.

12. A composition of claim 4 including about 90% N-acetyl-p-aminophenol; about 6.4% partially gelatinized starch; about 0.15% by weight stearic acid; about 1.2% polyvinylpyrrolidone and about 2.2% cross-linked povidone.

13. The composition of claim 5 wherein the composition is at least substantially free of fully gelatinized starch.

14. An orally administerable analgesic tablet formed from the composition of claim 1.

15. An orally administerable analgesic tablet formed from the composition of claim 12.

16. An orally administerable analgesic tablet formed from the composition of claim 6, 7, 8, 9, 10 or 11.

* * * * *